US011607490B2

(12) United States Patent
Richter et al.

(10) Patent No.: US 11,607,490 B2
(45) Date of Patent: Mar. 21, 2023

(54) VOLUME MEASURING ARRANGEMENT

(71) Applicant: Sanofi-Aventis Deutschland GmbH, Frankfurt am Main (DE)

(72) Inventors: Rene Richter, Tharandt (DE); Robert Witt, Frankfurt am Main (DE); Richard Guenther, Frankfurt am Main (DE); Thomas Nagel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 368 days.

(21) Appl. No.: 16/346,427

(22) PCT Filed: Oct. 30, 2017

(86) PCT No.: PCT/EP2017/077735
§ 371 (c)(1),
(2) Date: Apr. 30, 2019

(87) PCT Pub. No.: WO2018/083056
PCT Pub. Date: May 11, 2018

(65) Prior Publication Data
US 2019/0275239 A1    Sep. 12, 2019

(30) Foreign Application Priority Data

Nov. 1, 2016   (EP) .................................... 16196677

(51) Int. Cl.
*A61M 5/168*   (2006.01)
*A61M 5/315*   (2006.01)
(Continued)

(52) U.S. Cl.
CPC ............ *A61M 5/1684* (2013.01); *A61M 5/14* (2013.01); *A61M 5/168* (2013.01);
(Continued)

(58) Field of Classification Search
CPC ...... A61M 5/1684; A61M 2005/14513; A61M 5/14; A61M 5/168; A61M 5/31535;
(Continued)

(56) References Cited

U.S. PATENT DOCUMENTS 2,680,439 A * 6/1954 Sutermeister ........... A61M 5/30
604/70
3,308,818 A * 3/1967 Rutkowski .............. A61M 5/30
102/512
(Continued)

FOREIGN PATENT DOCUMENTS

CN     1308551     8/2001
CN     1321096     11/2001
(Continued)

OTHER PUBLICATIONS

International Preliminary Report on Patentability in Application No. PCT/EP2017/077735, dated May 7, 2019, 7 pages.
(Continued)

*Primary Examiner* — Nilay J Shah
(74) *Attorney, Agent, or Firm* — Fish & Richardson P.C.

(57) ABSTRACT

The present disclosure relates in one aspect to a measuring arrangement for measuring a volume occupied by a liquid medium inside a liquid reservoir, the measuring arrangement including a container having an interior volume containing a gas reservoir filled with a gaseous medium and containing a liquid reservoir filled with a liquid medium, wherein the gas reservoir and the liquid reservoir are hermetically separated by an impenetrable separation wall, a volume modulator to induce a volume change of the gas reservoir, a pressure sensor arranged inside the gas reservoir to measure a pressure change of the gaseous medium in response to the volume change of the gas reservoir, and a controller connectable to the pressure sensor, wherein the controller is
(Continued)

configured to calculate the volume of the liquid reservoir on the basis of the pressure change and the volume change.

15 Claims, 2 Drawing Sheets

(51) Int. Cl.
*A61M 5/48* (2006.01)
*G01F 22/02* (2006.01)
*A61M 5/14* (2006.01)
*A61M 5/142* (2006.01)
*A61M 5/145* (2006.01)
*A61M 5/20* (2006.01)
*G01F 17/00* (2006.01)
*G01F 22/00* (2006.01)

(52) U.S. Cl.
CPC ........ *A61M 5/31535* (2013.01); *A61M 5/486* (2013.01); *G01F 22/02* (2013.01); *A61M 5/2053* (2013.01); *A61M 2005/14268* (2013.01); *A61M 2005/14513* (2013.01); *A61M 2205/3331* (2013.01); *A61M 2205/3379* (2013.01); *A61M 2205/3389* (2013.01); *G01F 17/00* (2013.01); *G01F 22/00* (2013.01)

(58) Field of Classification Search
CPC ................ A61M 5/486; A61M 5/2053; A61M 2005/14268; A61M 2205/3331; A61M 2205/3379; A61M 2205/3389; A61M 2205/3382; A61M 2205/3386; G01F 22/02; G01F 17/00; G01F 22/00
See application file for complete search history.

(56) References Cited

U.S. PATENT DOCUMENTS

| | | | |
|---|---|---|---|
| 3,894,538 A | 7/1975 | Richter et al. | |
| 4,808,161 A * | 2/1989 | Kamen | A61M 5/16809 604/67 |
| 4,976,162 A | 12/1990 | Kamen | |
| 5,823,991 A * | 10/1998 | Shim | A61M 5/14276 604/500 |
| 5,859,365 A | 1/1999 | Kataoka et al. | |
| 5,935,105 A * | 8/1999 | Manning | A61M 5/16809 604/122 |
| 6,321,597 B1 | 11/2001 | Demera et al. | |
| 6,348,043 B1 * | 2/2002 | Hagen | A61M 5/1452 604/131 |
| 6,604,908 B1 * | 8/2003 | Bryant | A61M 1/367 417/26 |
| 2003/0136189 A1 * | 7/2003 | Lauman | A61M 1/287 73/304 C |
| 2005/0069425 A1 * | 3/2005 | Gray | A61M 1/267 417/392 |
| 2009/0035152 A1 * | 2/2009 | Butterfield | A61M 5/14224 417/53 |
| 2009/0131863 A1 | 5/2009 | Carlisle et al. | |
| 2010/0102799 A1 | 4/2010 | Schnidrig | |
| 2011/0071465 A1 * | 3/2011 | Wang | A61M 1/16 604/67 |
| 2013/0204205 A1 | 8/2013 | Horlock | |
| 2013/0237955 A1 | 9/2013 | Neta et al. | |
| 2014/0216560 A1 | 8/2014 | Ambrosina et al. | |
| 2014/0276409 A1 | 9/2014 | Rosinko et al. | |

FOREIGN PATENT DOCUMENTS

| | | |
|---|---|---|
| CN | 101432601 | 5/2009 |
| CN | 101721761 | 6/2010 |
| CN | 103017852 | 4/2013 |
| CN | 104602735 | 5/2015 |
| CN | 104870035 | 8/2015 |
| CN | 105163776 | 12/2015 |
| CN | 105246526 | 1/2016 |
| CN | 105258760 | 1/2016 |
| CN | 105288772 | 2/2016 |
| CN | 105764544 | 7/2016 |
| EP | 0622615 | 11/1994 |
| JP | H01-016426 | 1/1989 |
| JP | H05-502096 | 4/1993 |
| JP | H09-280920 | 10/1997 |
| JP | H10-068648 | 3/1998 |
| JP | 2004-275466 | 10/2004 |
| JP | 2010-269648 | 12/2010 |
| JP | 2011-158378 | 8/2011 |
| JP | 2012-225786 | 11/2012 |
| JP | 2012-527272 | 11/2012 |
| JP | 2014-020822 | 2/2014 |
| JP | 2016-512972 | 5/2016 |
| JP | 2016-540579 | 12/2016 |
| KR | 20140118453 | 10/2014 |
| WO | WO 1990/013795 | 11/1990 |
| WO | WO 2000/002606 | 1/2000 |
| WO | WO 2001/021234 | 3/2001 |
| WO | WO 2007/094833 | 8/2007 |
| WO | WO 2010/145908 | 12/2010 |
| WO | WO 2014/005955 | 1/2014 |
| WO | WO 2014/102259 | 7/2014 |
| WO | WO 2014/123816 | 8/2014 |
| WO | WO 2014/150157 | 9/2014 |
| WO | WO 2014/158627 | 10/2014 |
| WO | WO 2015/063462 | 5/2015 |
| WO | WO 2015/091761 | 6/2015 |

OTHER PUBLICATIONS

International Search Report and Written Opinion in Application No. PCT/EP2017/077735, dated Jan. 2, 2018, 13 pages.

* cited by examiner

VOLUME MEASURING ARRANGEMENT

CROSS REFERENCE TO RELATED APPLICATIONS

The present application is the national stage entry of International Patent Application No. PCT/EP2017/077735, filed on Oct. 30, 2017, and claims priority to Application No. EP 16196677.5, filed on Nov. 1, 2016, the disclosures of which are incorporated herein by reference.

TECHNICAL FIELD

The present disclosure relates to the field of measurement devices and measurement methods, in particular to a measurement arrangement and to a respective method configured to measure a volume occupied by a liquid medium inside a reservoir. In another aspect the disclosure relates to a drug delivery device equipped with such a measuring arrangement.

BACKGROUND

Syringe systems or infusion systems are typically used for parenteral administering of liquid drugs or medicaments. Especially for patients suffering a chronic disease a regular and repeated delivery of a liquid medicament is of importance. Liquid medicaments commonly delivered via injection or via intravenous infusion. For various types of medicament delivery there exist particular drug delivery devices, such as injectors or infusion pumps. With such devices the medicament itself is typically stored and provided in a separate container. With syringe type injection devices the liquid medicament is for instance provided in a cartridge having a tubular-shaped barrel which is sealed at one longitudinal end by a pierceable septum and which is sealed at the opposite longitudinal end by means of a piston or stopper which is slidably displaceable inside the barrel.

By means of a suitable drive mechanism, typically including an advancing piston rod, the piston or stopper of the cartridge is displaceable towards a distal direction so as to expel a predefined amount of the liquid medicament from the cartridge. For this the the pierceable septum is typically pierced and penetrated by a hollow injection needle.

Other medicament delivery systems and devices, such as infusion pumps make use of a tubing in fluid communication with e.g. a flexible container or flexible reservoir containing the liquid medicament. A pump, such as a peristaltic pump may feed a well-defined amount of the medicament by way of suction. Suction pump-based drug delivery devices require a complete flushing of the tubing that extends between the medicament container and an outlet end of the tubing, which may be in direct fluid communication with biological tissue that should be subject to medicament delivery.

Especially with infusion pumps or comparable pump based medicament delivery systems the tubing connecting a piercing element, such as a hollow cannula, and the medicament container or reservoir must be void of any air- or gas bubbles. So before the drug delivery device is deployed and activated for medicament delivery the device and hence the tubing in fluid communication with the medicament container must be completely flushed or flooded in order to ensure, that any air or gas initially contained in an empty tubing has been expelled therefrom.

The size of containers pre-filled with a liquid medicament may also be subject to inevitable tolerances. In addition to that the lumen of a tubing connected to a container may vary and may exhibit different sizes. The amount of medicament required to completely flush a tubing may be subject to rather large fluctuations. The amount of medicament that is needed to flush or to flood a tubing, hence to prime the tubing of a drug delivery device prior to its intended use, may therefore vary. For some application purposes and for some drug delivery devices it is desirable to precisely determine the volume of the liquid medicament contained in a container or reservoir prior to or during a process of medicament delivery to a patient.

Some drug delivery devices may be equipped with an electronic controller by way of which the amount of medicament dispensed over time can be precisely monitored. At some instance replacement of an empty medicament container may be due. Having precise knowledge of the filling volume of the container the time or time interval at which a change of a container becomes due can be precisely determined beforehand.

It is therefore an object of the present disclosure to provide a measuring arrangement for measuring a volume occupied by a liquid medium inside a reservoir that provides measuring of the volume with high precision. The measuring arrangement should be rather easy to implement. It should be implementable in a space saving and cost efficient way. Moreover, the measuring arrangement should be universally applicable for different types of reservoirs configured to contain a liquid medium or liquid substance such as a liquid medicament. The measuring arrangement should be further combinable with and should be implementable into a drug delivery device, such as an infusion pump. The measuring arrangement should provide a precise measurement of a volume occupied by a liquid medium at any time prior to or during a process of medicament delivery. It is a further object to provide a method of measuring a volume occupied by a liquid medium inside a reservoir.

SUMMARY

In one aspect a measuring arrangement for measuring of a volume occupied by a liquid medium inside a reservoir is provided. The measuring arrangement comprises a container having an interior volume containing a gas reservoir and containing a liquid reservoir. The gas reservoir is filled with a gaseous medium. The liquid reservoir is filled with a liquid medium. Typically, the gas reservoir is entirely filled with the gaseous medium and the liquid reservoir is entirely filled with the liquid medium, such as a liquid drug or medicament. The gas reservoir and the liquid reservoir are further hermetically separated by an impenetrable separation wall. Hence, the separation wall is impenetrable for the gaseous medium of the gas reservoir as well as for the liquid medium contained in the liquid reservoir.

The measuring arrangement further comprises a volume modulator to induce a volume change of the gas reservoir. The measuring arrangement also comprises a pressure sensor arranged inside the gas reservoir to measure a pressure change of the gaseous medium in response to the volume change of the gas reservoir, e.g. induced by the volume modulator. In addition, the measuring arrangement comprises a controller that is connectable to the pressure sensor. The controller is configured to calculate the volume of the liquid reservoir on the basis of the pressure change and the volume change.

The gas reservoir and the liquid reservoir are portions of the interior volume of the container. Typically, the gas reservoir and the liquid reservoir are both entirely located inside the interior volume of the container. In some embodiments the interior volume of the container consists of the gas reservoir and the liquid reservoir. In other words, the interior volume of the container may be divided into the gas reservoir and the liquid reservoir. Gas and liquid reservoir may only be separated by a separation wall. The container is typically closed to the exterior. Especially the liquid reservoir may be substantially closed or locked so that the liquid medium contained therein cannot escape therefrom.

Typically, the gas reservoir, in particular a portion of its boundary is in direct mechanical contact with the liquid reservoir, hence with a boundary of the liquid reservoir. The impenetrable separation wall may form at least a portion of the boundary of the liquid reservoir as well as a portion of the boundary of the gas reservoir. It is even conceivable that the impenetrable separation forms or constitutes a boundary of the liquid reservoir entirely surrounded by the gas reservoir.

The gas reservoir is that volumetric component of the interior volume of the container that is filled with a gaseous medium and the liquid reservoir is the respective volumetric component of the interior volume of the container that is filled with the liquid medium. Due to the separation of the gas reservoir from the liquid reservoir by means of the at least one separation wall, a mixing of the gaseous medium and of the liquid medium is effectively prevented.

The measuring arrangement and the method of measuring a volume occupied by the liquid medium is based on the assumption that the gaseous medium behaves as an ideal gas at a constant temperature. Furthermore it is assumed, that the liquid reservoir and hence the liquid medium entirely filling the liquid reservoir is substantially incompressible, at least compared to the compressibility of the gaseous medium in the gas reservoir.

The volume modulator of the measuring arrangement is configured to modify the volume of the gas reservoir of the container without any exchange of the liquid medium or gaseous medium contained inside the interior volume of the container. The volume modulator is configured to induce a volume change of the gas reservoir without affecting the volume of the liquid reservoir.

If for instance the volume of the gas reservoir is decreased by the volume modulator the pressure inside the gas reservoir will increase due to a compression of the gaseous medium, which is a consequence of the change of volume of the gas reservoir. Since the liquid medium and hence the liquid reservoir is substantially incompressible the reduction of the volume of the gas reservoir leads to an increase of the gas pressure therein.

This pressure increase can be measured by means of the pressure sensor. The measured pressure change is directly indicative of the total volume of the gas reservoir given that the volume change inducible by the volume modulator is either constant and fixed or is variably but known to the controller. The relation of a pressure change at a given volume change of the gas reservoir is directly indicative of the total volume of the gas reservoir. The interior volume of the container is always constant and is composed of the volume of the gas reservoir and the volume of the liquid reservoir. Then, the volume of the liquid reservoir can be easily calculated by subtracting the volume of the gas reservoir from the interior volume of known size.

The smaller the volume of the gas reservoir is the larger will be a pressure change in response to a volume change of the gas reservoir. Hence, when the liquid reservoir is rather large and when for instance a major portion of the interior volume is occupied by the liquid reservoir and/or with the liquid medium a volume change of the gas reservoir will immediately lead to a respective pressure change of the gaseous medium in the gas reservoir. With a comparatively small liquid reservoir, e.g. when the liquid medium has been withdrawn or expelled therefrom the pressure level in the gas reservoir may constantly drop as the volume of the gas reservoir increases.

A pressure change, in particular an increase of the gas pressure inside the gas reservoir induced by the volume modulator may then have a smaller impact on a change of the gas pressure inside the gas reservoir. With the above given assumptions of an almost ideal gas behavior of the gaseous medium in the gas reservoir and with the further assumption that the liquid medium is substantially incompressible the volume of the liquid reservoir can be precisely expressed by a formula with the volume change and with the measureable pressure change as variables and with the total interior volume and with an initial pressure as known parameters.

In some embodiments the controller is permanently connected to the pressure sensor. It may thus continuously monitor a pressure level sensed by the pressure sensor. In other embodiments the controller is only frequently connected to the pressure sensor. Then, signals provided by the sensor will be processed only at given predefined times or on demand, e.g. when a user or some other electronic device in communication with the controller demands or triggers a volumetric measurement of the liquid reservoir. A communication link between the controller and the pressure sensor may be wired or corded.

Alternatively, the communication link between the pressure sensor and the controller may be of wireless type. Then, the pressure sensor and the controller each comprise at least one of a wireless receiver, a wireless transmitter and a wireless transducer. Alternatively, at least one of the controller and the pressure sensor may be connected in a signal transmitting way with at least one of a wireless receiver, a wireless transmitter and a wireless transducer. The wireless communication link may be based on any kind of available wireless communication standard, such as Bluetooth, IEEE 802.11(Wi-Fi, WLan) or RFID, just to mention a few.

A wireless connection between the controller and the pressure sensor enables a somewhat arbitrary positioning of the controller relative to the pressure sensor. Hence, the controller may be arranged inside or at an outside of a housing of a drug delivery device equipped with the measuring arrangement. Alternatively and with a wireless communication link the controller may be located inside another electronic device capable to communicate with the pressure sensor.

Here, the controller or its function may be provided by an external electronic device, such as a smartphone, a tablet computer or any other kind of digital signal processing device.

The measuring arrangement is of particular use for liquid reservoirs that have a rather complex or non-constant, e.g. a rather flexible shape making a conventional volumetric measurement rather difficult. Measuring of the volume of the liquid reservoir by a volume change of the adjoining gas reservoir and measuring of a respective gas pressure change is universally applicable for arbitrarily-shaped liquid reservoirs as long as the liquid reservoir is entirely arranged inside the interior volume of the container and as long as the liquid medium is locked inside the liquid reservoir during the volumetric measurement.

In an embodiment the volume modulator comprises a piston slidably arranged in a longitudinally extending guiding section of a sidewall of the container. The piston is typically sealed against the guiding section, so that the piston is displaceable along the guiding section in longitudinal direction without escape of the gaseous medium from the container as well as without ingress of a gaseous medium into the container from outside. The piston is sealed gas tight with regard to the guiding section. The guiding section may comprise a cylindrical portion integrated into or arranged adjacent to a sidewall of the container. In this way a longitudinal sliding motion of the piston relative to the guiding section of the sidewall of the container leads to a volume increase or volume decrease of the gas reservoir of the container.

Typically, the guiding section of the container has a constant diameter that matches with the respective diameter or cross section of the piston. The guiding section may comprise a tubular shaft and the piston may comprise a tubular or circular-shaped polymeric or elastomeric stopper sealed against the shaft-shaped guiding section. During a volumetric measurement the piston is typically moved along the longitudinally extending guiding section for a well-defined displacement distance. Having knowledge of the length of the displacement of the piston and of the piston's and the guiding section's cross-section or diameter, the volume change due to the piston's displacement relative to the longitudinally extending guiding section can be precisely determined. Here, from a known or measureable longitudinal displacement path of the piston a resulting volume change can be calculated.

The resulting pressure change of the gaseous medium inside the gas reservoir is measured by the pressure sensor. Respective measurement signals are transmitted and provided to the controller to calculate the volume of the liquid reservoir on the basis of the measured pressure change, the volume change, the given interior volume of the container and an initial pressure of the gas reservoir, i.e. before the volume change was induced by the volume modulator.

Implementation of the volume modulator by means of a piston longitudinally displaceable along a correspondingly extending guiding section is only one approach to modify the volume of the gas reservoir in order to induce a pressure change of the gaseous medium contained therein. By means of a longitudinally displaceable piston the volume change can be easily and precisely determined.

According to another embodiment the piston is displaceable along the guiding section by means of a drive. Typically, the drive is operable by a regulator. The drive may be implemented as an electric drive, which may be mechanically coupled to the piston by means of a suitable gear or gearbox. The drive and its mechanical connection to the piston may provide a rather precise longitudinal movement of the piston relative to the guiding section. Control of the drive by means of the regulator may even provide different levels of displacement or different displacement distances of the piston. The mechanical connection between the drive and the piston is well known so that the duration of operation of the drive and/or a number of revolutions of the drive is directly indicative of the magnitude of longitudinal displacement of the piston along the guiding section.

In some embodiments the regulator may coincide with the controller. In other embodiments, the controller and the regulator are implemented as separate devices or electronic processing units. When implemented as separate devices or units the controller and the regulator may be connected in a signal transmitting way. By operating the piston by means of a drive that is itself operable by the regulator and by connecting the regulator to the controller the controller itself may even induce different and/or multiple volume changes of the gas reservoir. In this way, multiple measurement procedures may be conducted, each of which on the basis of a different volume change. In combination with the corresponding pressure changes the volume of the liquid reservoir can be calculated several times, so that an average value for the volume of a liquid reservoir can be obtained. In this way, the precision of the measuring arrangement and of the respective method of measuring can be enhanced.

According to another embodiment the liquid reservoir is in fluid connection with an outlet extending through the container. The outlet is typically connected with that side of the liquid reservoir facing away the separation wall, hence facing away the gas reservoir. During a measurement procedure the outlet is blocked or locked. Otherwise and if the liquid medium could escape from the liquid reservoir during a volumetric measurement the precision of the volume measurement may suffer. Providing the liquid reservoir with an outlet enables withdrawal of the liquid medium, e.g. the liquid medicament, directly from the liquid reservoir for medicament delivery by means of a drug delivery device, e.g. equipped with the measuring arrangement.

In another embodiment the outlet of the liquid reservoir is selectively lockable by a control valve and/or by a suction pump. Selectively locking or blocking of the outlet by at least one of a control valve and a suction pump enables a precise volumetric measurement of the volume of the liquid reservoir. The incompressible liquid medium cannot escape during the volumetric measurement. In this way, any volume change of the gas reservoir directly corresponds to a respective pressure change of the gaseous medium contained or entrapped therein. The control valve is an actively controlled valve. It may be switched into a locking or blocking mode, in which the control valve effectively blocks or locks the outlet of the liquid reservoir.

In this way the control valve can be controlled in a rather deterministic way and independent of a pressure level inside the outlet or inside the liquid reservoir. Additionally or alternatively also a suction pump may be in fluid communication with the outlet and may be hence in fluid communication with the liquid reservoir. The suction pump, e.g. a peristaltic pump or a piston pump may behave in a similar way as the control valve described above. The suction pump as well as the control valve may be in a normally closed configuration thereby blocking or locking any flow of the liquid medicament through the outlet and hence away from the liquid reservoir. When the suction pump provides a normally closed configuration of the outlet the suction pump may be exclusively installed instead of a control valve. Activating the suction pump would induce a flow of the liquid medium from the liquid reservoir. The deactivation of the suction pump or setting the suction pump into an idle mode would lock or block any fluid flow through the outlet and hence through a tubing in fluid communication with the liquid reservoir.

In another embodiment at least one of the control valve and the suction pump is connected with the regulator. At least one of the control valve and the suction pump is also controllable by the regulator either mechanically or electrically. When connected to the controller the regulator may trigger, conduct or initiate a volumetric measurement procedure of the liquid volume. Also, by means of an interaction or signal transmitting coupling between the controller and the regulator the controller may trigger, conduct or initiate a dispensing action, e.g. by manipulating at least one of the control valve and the suction pump.

In a first step of operation, the suction pump or the control valve, whichever is implemented in the measuring arrangement and is connected to the controller or regulator is switched into a normally closed configuration. Then, any fluid flow through the outlet or tubing is effectively blocked. Thereafter, the volume modulator may be triggered by the regulator or by the controller to induce a volume change, typically a decrease or an increase of the volume of the gas reservoir. This will immediately lead to an increase or decrease of the gas pressure inside the gas reservoir which is measured by the pressure sensor. The measured pressure change is provided to the controller via its connection to the at least one pressure sensor. After a calculation of the volume of the liquid reservoir the regulator or controller may restart the suction pump or may open the control valve so that the flow of the liquid medicament and hence delivery thereof may continue. It is only for a rather short time interval, that e.g. a constant fluid flow normally provided by the suction pump has to be interrupted and blocked so as to conduct a volumetric measurement of the liquid reservoir.

In another embodiment the volume occupied by the liquid medium $V_{fluid}$ is calculated as $$V_{fluid} = V_{total} - \Delta V \left( \frac{p_i}{\Delta p} + 1 \right),$$

with $V_{total}$ being the available or total interior volume of the container $\Delta V$ being the volume change of the gas reservoir $\Delta p$ being the resulting pressure change inside the gas reservoir and $p_i$ being an initial pressure inside the gas reservoir, i.e. before the volume change was induced. This formula is immediately derived from the assumption, that the interior volume of the container is composed of the volume of the liquid reservoir and the volume of the gas reservoir and further by the assumption that the gaseous medium contained in the gas reservoir behaves like an ideal gas. Hence, a product of an initial pressure and an initial volume of the gas reservoir is equal to a product of a first pressure and a corresponding first volume of the gas reservoir that arises after the volume modulator induced a volume change thereof.

The above given formula for calculating the liquid medium is rather simple and can be easily implemented into the controller, typically configured as an electronic controller, such as a microcontroller. Computational demands for calculating of the volume of the liquid medium can therefore be kept on a rather low level, which is attractive for saving energy, especially when the measuring arrangement is configured as a mobile and battery-driven device.

In one embodiment the separation wall hermetically separating the gas reservoir and the liquid reservoir is flexible and/or stretchable. In some embodiments the separation wall may even be displaceable inside the interior volume of the container. When implemented displaceable the separation wall does not need to be flexible or stretchable. It may displace inside the interior volume like a piston or stopper in a cylindrical barrel of a cartridge typically filled with a medicament. The container is generally made of a pressure-resistant material. The container, in particular the sidewalls of the container entirely confining the gas reservoir and the liquid reservoir are typically non-flexible and non-stretchable. The container is made of a rather rigid material and comprises a constant unmodifiable geometric structure. A rather rigid and non-flexible container is of particular benefit for that any volume change of the gas reservoir leads to a respective and measurable pressure change of the gaseous medium inside the gas reservoir.

In another embodiment the liquid reservoir is formed by a flexible bag filled with the liquid medium. Typically, the liquid reservoir is completely sealed and forms an interior volume, which is completely confined by the sidewalls of a flexible bag. The separation wall between the liquid reservoir and the gas reservoir is then formed by the flexible bag. The liquid reservoir is typically entirely filled with the liquid medium, such as with a liquid medicament. The liquid reservoir is typically void of gas- or air bubbles. When formed or provided as a flexible bag the liquid reservoir is entirely contained and arranged inside the container. Only an outlet or a tubing in fluid connection with the interior of the liquid reservoir may extend through the container. By means of the control valve or by means of the above mentioned suction pump any fluid flow through such tubing or outlet can be selectively interrupted in order to conduct a volumetric measurement of the liquid reservoir.

When arranged inside the container the flexible bag forms the separation wall between the gas reservoir and the liquid reservoir. The liquid reservoir is entirely confined by flexible sidewall portions of the flexible bag. The flexible bag may even be entirely surrounded by the gas reservoir. The volumetric measurement can be conducted totally independent and irrespective of a specific geometric shape of the liquid reservoir and its flexible bag as long as the flexible bag is entirely filled with the liquid medium and as long as the flexible bag is in direct contact with the gas reservoir inside the container.

In another embodiment the liquid reservoir is formed in part by the container. Here, the impenetrable separation wall between the liquid reservoir and the gas reservoir comprises a flexible membrane or is even constituted by a flexible membrane. The flexible membrane may separate the interior volume of the container into a liquid chamber and into a gas chamber of the interior volume. The shape and position of the flexible membrane may change in accordance with the delivery of the liquid medicament from the liquid reservoir. Typically and in an initial configuration at least an outer border of the flexible membrane may be fixed to an inside facing sidewall portion of the container. As the liquid reservoir constantly empties a middle portion of the flexible membrane spaced apart from the outer border region thereof may be subject to a deformation towards the outlet of the container. The flexible membrane is just another embodiment of the impenetrable separation wall separating the liquid reservoir and the gas reservoir.

Arranging of a flexible membrane inside the container may be rather cost efficient and easy to manufacture. Here, the entire container with the flexible membrane and with the pressure sensor arranged inside the gas reservoir may be designed and configured as a disposable unit that is intended to be discarded in its entirety once the liquid medium has been withdrawn or expelled therefrom.

In embodiments with a flexible bag forming the liquid reservoir the flexible bag may be designed and configured as a disposable unit that is intended to be discarded in its entirety once the liquid medium has been withdrawn or expelled therefrom.

In another embodiment the container comprises at least a first container part and a second container part that are detachably connectable to form the interior volume. Here, the container is a multi-component container. First and second container parts are sealingly engageable and can be fixed and assembled to each other to form a liquid tight and gas tight interior volume. Separating the container into a first container part and a second container part might be useful to provide a reusable container part and a disposable container part. For instance, the first container part may be configured and designed as reusable container part that is repeatedly connectable with a second container part that is configured and designed as a disposable container part.

In this way, rather valuable components of the measuring arrangement, such as the pressure sensor, the control valve and/or the suction pump can be repeatedly used with various liquid reservoirs. Once the liquid content of a liquid reservoir has been used up the respective liquid reservoir together with, e.g. the second container part could be replaced by another, filled liquid reservoir and a second container part. The liquid reservoir and the second container part may thus be implemented as disposable components of the measuring arrangement and/or as disposable components of a drug delivery device. Once the content of the liquid reservoir has been used up or should no longer be used, it may be discarded together with the second container part. A new second container part equipped with a filled and new liquid reservoir may then replace the previous one.

In another embodiment the volume modulator and the pressure sensor are arranged in the first container part. Optionally, also the controller, the regulator as well as the control valve and/or the suction pump are arranged in or at the first container part. The first container part is typically configured as a reusable container part. Having the controller arranged or attached in or to the first container part enables a rather long term and comprehensive recording of the content of the liquid reservoir and/or of a series of liquid reservoirs. In addition, the most costly and valuable components of the measuring arrangement may be arranged in the reusable container part. The manufacturing costs for a disposable container part can therefore be decreased to a minimum.

According to another embodiment the liquid reservoir filled with a liquid medicament is arranged in the second container part. Optionally, the control valve may also be arranged or attached to the second container part. Arranging the liquid reservoir with the liquid medicament in the second container part, which is configured as a disposable container part, enables a one-time use of a disposable liquid reservoir. Once the liquid reservoir is empty it is discarded and replaced by a new one. In this way, refilling of an empty liquid reservoir can be avoided so as to decrease a potential risk of contamination of the liquid reservoir.

In another aspect a drug delivery device is provided that comprises a housing, a suction pump and a measuring arrangement as described above. The drug delivery device may be configured and implemented as an infusion pump or as an infusion system. Alternatively, the drug delivery device may be configured as an injection device, such as a syringe-type injection device.

Generally, the controller or regulator of the measuring arrangement may coincide with and may be provided by an electronic controller or regulator of the drug delivery device. Hence, the measuring arrangement may be entirely integrated into the drug delivery device. Implementing of a measuring arrangement as described above into a drug delivery device enables a precise volumetric measurement of a liquid reservoir filled with a liquid medium, in particular filled with a liquid medicament. At different stages of a medicament delivery process the medicament delivery may be temporally interrupted in order to conduct a volumetric measurement of the liquid reservoir and hence to conduct a volumetric measurement of the liquid medicament left inside the container.

In another embodiment at least one of the first container part and the second container part of the measuring arrangement as described above forms at least a portion of the housing of the drug delivery device. It is generally conceivable, that the housing of the drug delivery device comprises a first housing part that substantially coincides with the first container part as mentioned above and that the housing of the drug delivery device comprises a second housing part that substantially coincides with the second container part of the measuring arrangement as described above. In this way also the drug delivery device may be configured and designed as a multi-component device, wherein one component, namely the first housing component is reusable and wherein another housing component, hence the second housing component is configured and designed as a disposable component that is intended to be discarded in its entirety once the liquid medium contained therein has been used up or should no longer be used.

In order to conduct a volumetric measurement as described above the two housing components of the drug delivery device are sealingly engageable in a gas tight and fluid tight manner. The liquid reservoir may be provided in form of a flexible bag, which is entirely arranged inside an interior volume of the container which is composed of an assembly of the first housing component and the second housing component of the drug delivery device.

In another aspect a method of measuring a volume occupied by a liquid medium inside a reservoir, i.e. a liquid reservoir arranged inside a container is provided. The container further contains a gas reservoir filled with a gaseous medium. The method of measuring comprises the steps of inducing of a volume change of the gas reservoir, measuring of a pressure change in the gas reservoir in response to the volume change of the gas reservoir and calculating the volume of the liquid reservoir on the basis of the pressure change and the volume change.

Typically, calculation of the volume of the liquid reservoir is further conducted on the basis of the interior volume of the container, which is constant and known. The calculation of the volume of the liquid reservoir may be further conducted on the basis of an initial pressure, hence a pressure of and inside the gas reservoir prior to the induced volume change of the gas reservoir.

The method of measuring of the volume of the liquid medium is typically conducted by a measuring arrangement and/or by a drug delivery device as described above. It is to be noted, that any features, benefits and effects obtainable by the measuring arrangement as described above are equally valid for the method of measuring of a volume of a liquid medium; and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (02)25, Asp28] Exendin-4(1-39)-NH2,
des Pro36, Pro37, Pro38 [Met(O)14, Trp(02)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp (02)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and K. A light chain has two successive domains: one constant domain (CL) and one variable domain (VL). The approximate length of a light chain is 211 to 217 amino acids. Each antibody contains two light chains that are always identical; only one type of light chain, K or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the embodiments discussed herein without departing from the spirit and scope of the disclosure as defined in the appended claims. Further, it is to be noted, that any reference numerals used in the appended claims are not to be construed as limiting the scope of the disclosure.

BRIEF DESCRIPTION OF THE FIGURES

In the following, embodiments of the present disclosure will be described by making reference to the drawings, in which.

DETAILED DESCRIPTION

Figure 1:
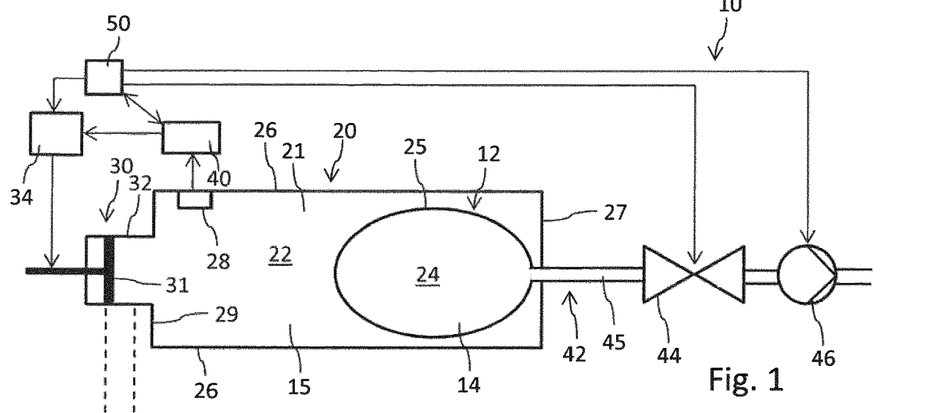
FIG. 1 is a schematic block diagram of a measuring arrangement in an initial configuration.
Figure 2:
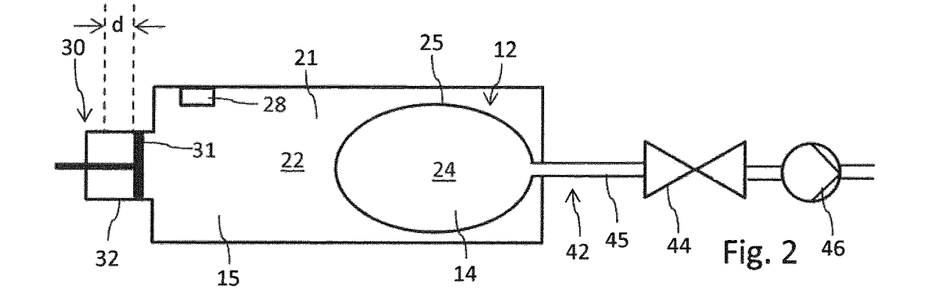
FIG. 2 is the measuring arrangement according to FIG. 1 with an induced volume change of a gas reservoir in comparison to the initial configuration of FIG. 1.

In FIGS. 1 and 2 an embodiment of the measuring arrangement 10 is schematically illustrated. The measuring arrangement 10 comprises a container 20 confining an interior volume 21. Inside the container 20 there is located a gas reservoir 22 filled with a gaseous medium 15. Inside the interior volume 21 there is further provided a liquid reservoir 24 filled with a liquid medium 14. The gas reservoir 22 and the liquid reservoir 24 are hermetically separated. In the embodiment according to FIGS. 1 and 2 the liquid reservoir 24 is confined and surrounded by a separation wall 25 that is impenetrable with regard to the gaseous medium 15 and with regard to the liquid medium 14. In the illustrated embodiment the separation wall 25 is flexible and/or deformable. The separation wall 25 forms a flexible bag 12 in which the liquid medium 14, e.g. a liquid medicament is stored.

Typically, the liquid medium 14 entirely fills the interior of the liquid reservoir 24. The liquid reservoir 24 is void of any air or gas bubbles. The liquid reservoir 24 is entirely located inside the interior volume 21 of the container 20. The container 20 has a rigid sidewall 26 as well as rigid end walls 27 and 29. Inside the gas reservoir 22 and hence inside the interior volume 21 but outside the liquid reservoir 24 there is located at least one pressure sensor 28. The pressure sensor 28 is configured to measure the gas pressure that is present inside the gas reservoir 22. The pressure sensor 28 is configured as an electric pressure sensor. It is configured to generate electric signals being indicative of a pressure level inside the gas reservoir 22. The pressure sensor 28 is connected to a controller 40. The controller 40 is configured to calculate the volume of the liquid reservoir 24 on the basis of a pressure change inside the gas reservoir 22 in response to a volume change of the gas reservoir 22.

In some embodiments, the container 20 may comprise a barrel made of glass or made of a vitreous material. In other embodiments the container 20 may comprise a plastic material, such as Cyclic Olefin Copolymer (COC) being substantially inert or nonreactive with regard to the liquid medium contained therein. Furthermore, the container 20 may comprise a cartridge made of plastic or glass.

The container 20 is further provided with a volume modulator 30 that is configured to induce a volume change of the gas reservoir 22. In the presently illustrated embodiment the volume modulator 30 comprises a piston 31 that is slidably arranged in a longitudinally extending guiding section 32 of the sidewall 26 or of an end wall 29 of the container 20. The guiding section 32 may comprise a cylindrical shaft or a cylindrical portion in which the piston 31 is slidably arranged. By displacing the piston 31 along the elongation of the guiding section 32 the interior volume 21, in particular the volume of the gas reservoir 22 can be modified in a well-defined and known way. Hence, the cartridge formed by the container 20 may be sealed by the piston 31.

In the illustration according to FIG. 2 the piston 31 has moved inwardly compared to its initial position of FIG. 1. As illustrated the piston 31 has moved by a distance d compared to its initial position according to FIG. 1. With a known cross-section of the piston 31 the volume change of the gas reservoir 22 can be calculated from a displacement d of the piston 31 the volume change is known for a known displacement d of the piston 31. The volume change is equal to the cross-section of the piston 31 multiplied by the distance d. Since the liquid reservoir 24 is entirely filled with a substantially incompressible liquid medium 14 the volume change induced by the volume modulator 30 leads to a well-defined change of the gas pressure inside the gas reservoir 22. As the interior volume 21 is for instance decreased by means of the volume modulator 30 the pressure will increase. As the volume of the container 20 and hence the volume of the gas reservoir 22 is increased the pressure will decrease. This pressure modification is detectable and quantitatively measurable by the pressure sensor 28. From the following relation $$V_{fluid} = V_{total} - \Delta V\left(\frac{p_i}{\Delta p} + 1\right)$$

the volume of the liquid reservoir 24 and hence the volume occupied by the liquid medium 14 can be precisely calculated.

The above given formula for calculating the volume of the liquid medium is based on the assumption that the liquid medium 14 is substantially incompressible, that the liquid reservoir 24 is free of any gas bubbles and that the volume change induced by the volume modulator 30 does not affect or modify the temperature of the gaseous medium 15 and that the gaseous medium 15 behaves like an ideal gas at a constant temperature. Hence, an initial pressure of the gas reservoir 22 multiplied with an initial volume of the gas reservoir 22 is equal to a modified volume thereof multiplied by the modified pressure that arises due to the volume change.

As indicated in FIG. 1 the volume modulator, hence the piston 31 is optionally coupled or connected to a drive 34 that is operable by the controller 40 and/or that is operable by a separate regulator 50. By means of a controller- or regulator-operated drive 34 the displacement of the piston 31 and hence the change of the interior volume 21 can be controlled by the controller 40 or regulator 50. Controller 40 and regulator 50 may be provided as separate devices or as separate electronic entities or units. In some embodiments the controller 40 and the regulator 50 may coincide. Then, the functionality of the regulator 50 is entirely implemented into the controller 40. A separate implementation of controller 40 and regulator 50 provides the possibility to arrange the controller 40 at a remote location, e.g. at or on an outside of a drug delivery device 1 or even to position the controller 40 within a predefined spatial range but at a certain distance from the drug delivery device 1.

In this way the controller 40 or regulator 50 may be configured to induce a quasistatic change of the interior volume 21 while the controller 40 simultaneously monitors a resulting pressure change. By means of the regulator-operated drive 34 and the regulator-operated volume modulator 30 the regulator 50 may deterministically modify the interior volume 21. Here, it is conceivable that the regulator 50 is controlled and/or triggered by the controller 40. The operation of the drive 34 and hence the displacement of the piston 31 controlled by the regulator 50 is directly indicative of the volume change induced by the volume modulator 30, e.g. by the piston 31. The calculation of the volume of the liquid reservoir 24 may be executed and conducted multiple times with different volume changes of the gas reservoir 22. In this way, a series of liquid reservoir volumes can be calculated, thus enabling calculation of an average volume of the liquid reservoir 24 thereby increasing the precision of the measurement and calculation.

As further illustrated in FIGS. 1 and 2 the liquid reservoir 24 is in fluid connection with an outlet 42 that extends through the container 20. Here, the outlet 42 comprises a tubing 45 in fluid communication with the interior of the liquid reservoir 24. The tubing 45 extends through an end wall 27 of the container 20. The container 20 is pressure-resistant and does not change its shape or geometry when a volume change of the gas reservoir 22 is induced by means of the volume modulator 30. The tubing 45 is further connected to a control valve 44 and to a suction pump 46. The control valve 44 and/or the suction pump 46 may be also connected to the regulator 50. The control valve 44 is actively controllable. Here, the regulator 50 may control opening and closing of the control valve 44. Moreover, the regulator 50 may also control operation of the suction pump 46.

The suction pump 46 and the control valve 44 are arranged in line or in series. The tubing 45 extends through the control valve 44 and then through the suction pump 46 or vice versa. The control valve 44 and/or the suction pump 46 may be controlled by the regulator 50. In this way any fluid flow from the liquid reservoir 24 can be controlled by the regulator 50. Both, the control valve 44 and the suction pump 46 may be in a normally closed configuration in the absence of a control signal from the regulator 50. In this way a fluid path through the outlet 42 and hence through the tubing 45 is normally blocked or locked. In this configuration a volumetric measurement of the volume occupied by the liquid medium 14 and hence a volumetric measurement of the liquid reservoir 24 can be conducted. Once the volumetric measurement has been completed the regulator 50, e.g. triggered by the controller, 40 may open the control valve 44 and may operate the suction pump 46.

Figure 3:
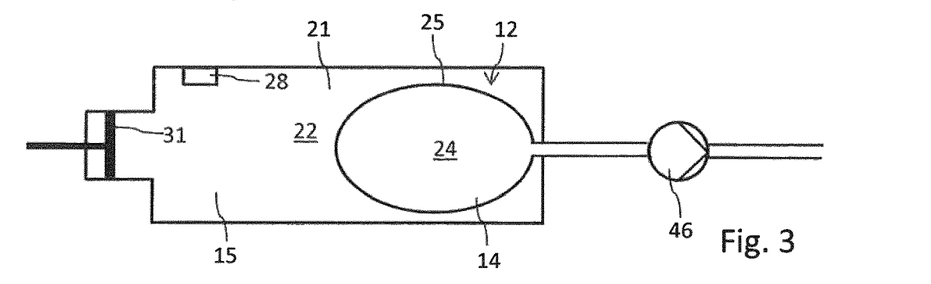
FIG. 3 is another embodiment of the measuring arrangement according to FIGS. 1 and 2.

In the embodiment according to FIG. 3 the functionality of the control valve 44 is completely provided by the suction pump 46. Here, the suction pump 46 is normally closed when deactivated, hence when a controller signal from the regulator 50 is absent. Apart from that the embodiment according to FIG. 3 is rather identical to the embodiment according to FIGS. 1 and 2. Only for reasons of simplicity the drive 34 is not separately illustrated in FIGS. 2 and 3.

Figure 4A:
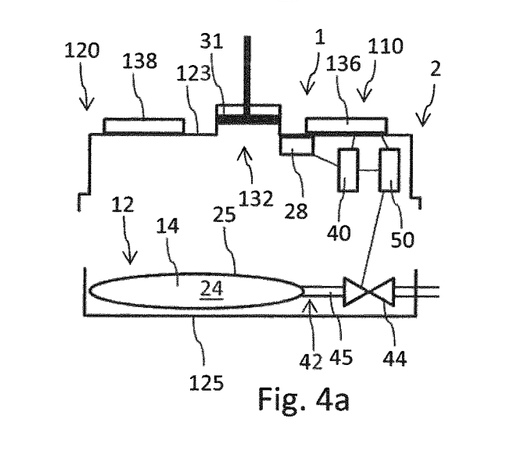
FIG. 4a shows a drug delivery device with a first and with a second housing component in a detached configuration.
Figure 4B:
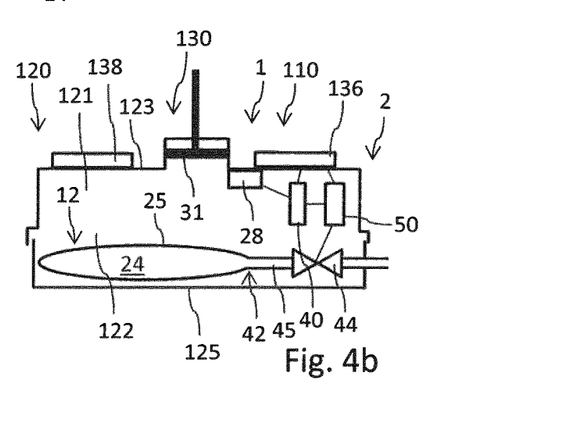
FIG. 4b shows the drug delivery device according to FIG. 4a in an assembled configuration.

In FIGS. 4a and 4b another embodiment of the measuring arrangement 110 is illustrated. Here, the measuring arrangement 110 is integrated into a drug delivery device 1. The drug delivery device 1 comprises a housing 2. The measuring arrangement 110 included and integrated into the drug delivery device 1 comprises a container 120 that may form the housing 2 of the drug delivery device 1. In other embodiments the container 120 may be arranged inside the housing 2 or may only form a part of the housing 2.

The container 120 of the measuring arrangement 110 comprises a first container part 123 and a second container part 125. As shown in FIGS. 4a and 4b the first and the second container parts 123, 125 are releasably and detachably connectable so as to form a closed container 120 or to form a closed housing 2 of the drug delivery device 1 having an interior volume 121. In the present embodiment the second container part 125 is provided with the liquid reservoir 24 and hence with a flexible bag 12 containing the liquid medicament 14. The liquid reservoir 24 is entirely surrounded by the gas reservoir 122 which is located inside the closed container 120.

Here, the liquid reservoir 24 may comprise a rather flat flexible bag 12 thus allowing a rather compact design of first and second container parts 123, 125 to form a rather compact housing 2 of the drug delivery device 1. The first container part 123, illustrated as an upper container part is equipped with the pressure sensor 28. Optionally and as shown in FIGS. 4a and 4b, also the controller 40 may be located inside the first container part 123. In other embodiments, the controller 40 may be attached or assembled to the first container part 123. It may be arranged on the outside of the first container part 123.

The controller 40 may be also located at least partially inside the first container part 123. Hence, a portion of the controller 40 may be located inside the first container part 123 and another portion of the controller 40 may extend through a sidewall of the first container part 123. Then, the controller 40 might by directly operable by a user of the device 1.

With other embodiments it is also conceivable that the controller 40 is located outside the drug delivery device 1 and that an signal transmitting connection between the pressure sensor 28 and the controller 40 is established by a wireless communication link, e.g. according to some type of wireless communication standard, such as Bluetooth, IEEE 802.11(Wi-Fi, WLan) or RFID. It is even conceivable that the controller 40 is implemented in an external electronic device, e.g. in a mobile electronic device, such as a smartphone or a tablet computer (not illustrated). The controller 40 may be implemented purely by software when provided or deployed by an external electronic device.

For a wireless communication link between the pressure sensor 28 and the controller 40, both the controller 40 and the pressure sensor 28 are equipped with at least one of a wireless receiver, a wireless transmitter and a wireless transceiver.

The first container part 123 may be further equipped with a volume modulator 130 and with a respective piston 31 guided in a, e.g. cylindrically-shaped shaft-like guiding section 132. Even though not illustrated the first container part 123 may be further equipped with an electric drive 34 and/or with a suction pump 46 as described in connection with the embodiment according to FIG. 1. Activation of the volume modulator 130 and/or displacement of the piston 31 along the guiding section 132 induces a volume change of the gas reservoir 122 as described above in connection with FIGS. 1 to 3 which leads to a change of the pressure inside the gas reservoir 122 that is measureable by the pressure sensor 28.

In typical embodiments the second container part 125 may be configured as a disposable container part whereas the first container part 123 may be configured as a reusable container part. The liquid reservoir 24 and hence the flexible bag 12 connected to or integrally formed with the outlet 42 and the tubing 45 may be pre-arranged or pre-packed in the second container part 125.

The control valve 44 may be optionally contained in the second container part 125. The control valve, e.g. in form of a clamp to block a liquid flow through the tubing 45 or outlet 42 may be also arranged inside or may be attached to the first container part 123. The suction pump 46 may be also integrated into the first container part 123. In this way, all reusable and valuable components of a drug delivery device 1 and/or of a measuring arrangement 110 are all provided inside or are attached to the first container part 123. In this way the costs for manufacturing the disposable second container part 125 can be decreased to a minimum.

With a one-time usable second container part 125 pre-configured with the liquid reservoir 24 and typically in fluid communication with the outlet 42 and/or the tubing 45 all fluid guiding components of the measuring arrangement 110 and/or of the drug delivery device 1 that get in direct contact with the liquid medium 14 are configured as disposable components, which after delivery of the liquid medium 14 are intended to be discarded. All other components of the drug delivery device 1 do not get in contact with the liquid medium 14 and hence with the liquid medicament 14.

The drug delivery device 1 as illustrated in FIGS. 4a and 4b may be further provided with a display 136 and with an actuation member 138 as well as with a regulator 50. Here, the regulator 50 is configured to control operation of the suction pump 46 and/or to control operation of the control valve 44. The actuation member 138 is configured as an input unit allowing a user to control operation of the drug delivery device 1, especially to trigger and to modify the process of delivery of the medicament. The actuation member 138 is mechanically and/or electrically connected to the regulator 50 and/or to the controller 40. The regulator 50 is electrically and/or mechanically connected to at least one or both of the suction pump 46 and the control valve 44. The regulator 50 may be also connected to the controller 40. In this way measuring of a pressure change and calculating of a volume of the liquid reservoir 24 to be conducted by the controller 40 may be triggered by at least one of the regulator 50 and the actuation member 138.

The display 136 may provide information to a user of the device about the medicament delivery actually taking place and/or about a dosing or delivery history. By means of the actuation member 138, measuring of the volume of the liquid medicament located inside the device 1 could be triggered manually by a user. The measurement could be further triggered autonomously, e.g. by the controller.

Figure 5:
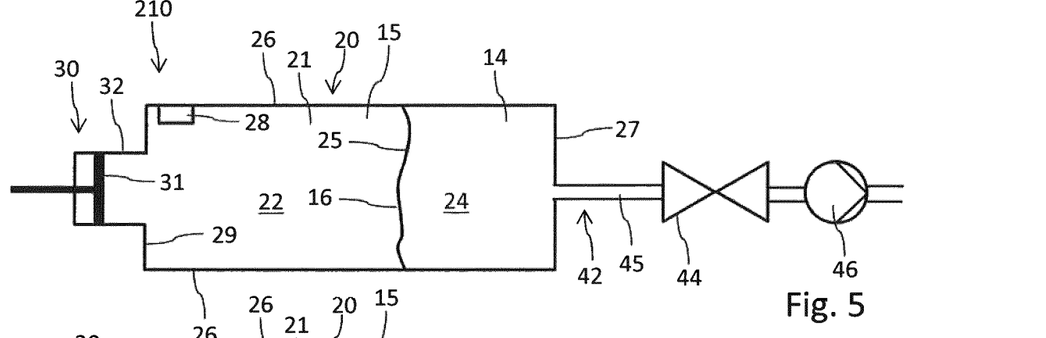
FIG. 5 shows another schematic block diagram of a measuring arrangement with a flexible membrane to separate the liquid reservoir and the gas reservoir in an initial configuration.
Figure 6:
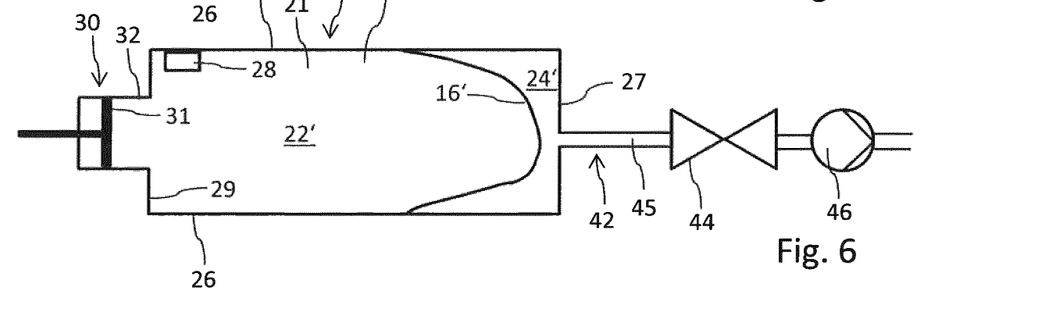
FIG. 6 shows the embodiment according to FIG. 5 after withdrawal and extraction of a portion of the liquid medium and FIG. 7 is a flowchart of the method of measuring a volume of a liquid medium.

In FIGS. 5 and 6 another embodiment of the measuring arrangement 210 is illustrated. The general structure and functionality of the measuring arrangement 210 according to FIGS. 5 and 6 is rather identical to the measuring arrangement 10 as described in connection to FIGS. 1-3. As far as not indicated otherwise identical components are denoted with identical reference numbers. Instead of a closed flexible bag 12 the liquid reservoir 24 is formed by a membrane 16 that is impenetrable for the gaseous medium 15 and for the liquid medium 14. As shown in an initial configuration according to FIG. 5 the membrane 16, typically implemented as a flexible membrane 16 is attached to the interior of a sidewall 26 of the container 20. The container 20 and hence its sidewall 26 may comprise a tubular shape. An outer circumference of the membrane 16 may be permanently and fixedly attached to the inside of the sidewall 26 of the pressure-resistant container 20.

As it is apparent from a comparison of FIGS. 5 and 6 the liquid medium 14 may be subject to withdrawal when the drug delivery device 1 is operated, e.g. by activation of the suction pump 46. As a consequence and since the liquid reservoir 24 is hermetically sealed to the gas reservoir 22 the volume of the liquid reservoir 24 will constantly decrease. The change of the size of the liquid reservoir 24 as shown in FIG. 5 decreases to a modified liquid reservoir 24' as illustrated in FIG. 6. At the same time the volume of the gas reservoir as initially shown in FIG. 5 increases to a modified volume of an enlarged gas reservoir 22'. The modification of the volumes of the liquid reservoir 24 and of the gas reservoir 22 leaves the total interior volume 21 of the container 20 unchanged. Consequently, the flexible membrane 16 is subject to a deformation. In the initial configuration of FIG. 5 the flexible membrane 16 is rather flat-shaped or even-shaped. As the liquid medium 14 is withdrawn from the liquid reservoir 24 the flexible membrane 16' is subject to a deformation.

In both configurations as shown in FIGS. 5 and 6 a volumetric measurement of the volume of the liquid medium 14 can be conducted in a way as described above. Also here, the liquid reservoir 24 is substantially void of any gas bubbles or gaseous components. It is entirely filled with the liquid medium 14. As the outlet 42 in fluid connection with the liquid reservoir 24 is blocked or obstructed, e.g. by the normally closed control valve 44 or by the normally closed suction pump 46 the volume modulator 30 may be activated in a way as described above. The displacement of the piston 31 induces a volume change of the gas reservoir 22 and further induces a measurable pressure change in the gas reservoir 22. In accordance to the above given formula the volume of the liquid reservoir 24 and hence the volume occupied by the liquid medium 14 can be calculated. In the embodiment according to FIGS. 5 and 6 the liquid reservoir 24 is at least partially confined by the container 20. A portion of the sidewall 26 and at least one of the end walls 27, 29 confine the liquid reservoir 24. With this embodiment the entire container 20 may be configured and designed as a disposable container that is intended to be discarded once the liquid medium 14 has been withdrawn therefrom.

Figure 7:
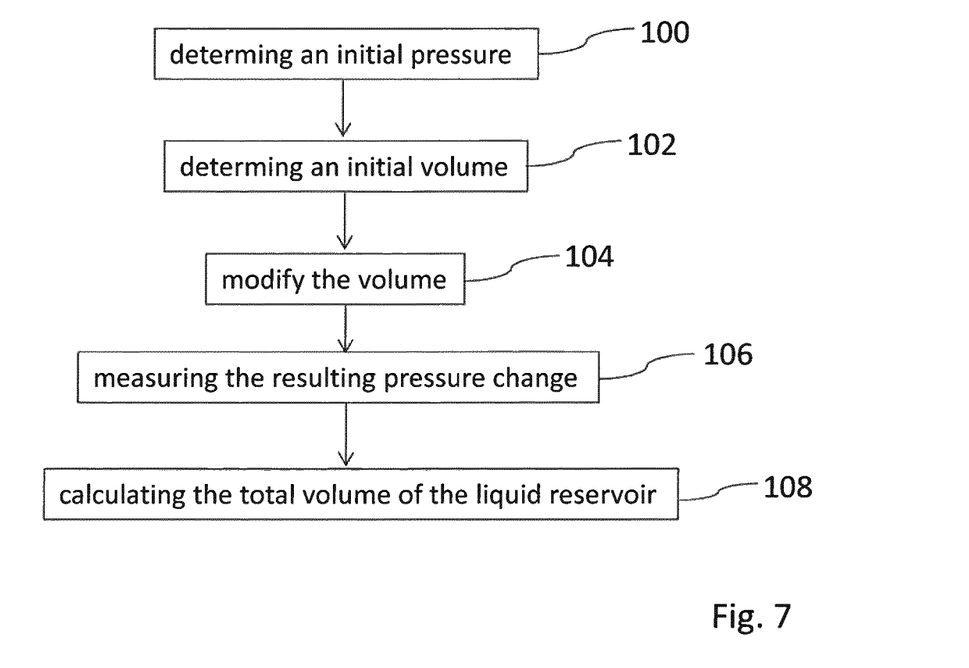

In FIG. 7 there is further given a flowchart of the method of measuring a volume occupied by the liquid medium 14 inside the liquid reservoir 24. In a first step 100 an initial pressure inside the gas reservoir 22 is determined, e.g. by means of the pressure sensor 28. In a further step 102 an initial volume, hence the volume of the container 20 is determined. The initial volume equals the total available interior volume of the entire container 20. Hence, the initial volume equals the sum of the volume of the gas reservoir and the volume of the liquid reservoir 22, 24. The initial volume is rather fixed and remains unchanged. It may be provided to the controller 40 or may be stored in the controlled 40 before volumetric measurement is conducted.

For measuring and for calculating the volume occupied by the liquid medium 14, hence for determining the volume of the liquid reservoir 24 in a subsequent step 104 the volume of the gas reservoir 22 is modified, typically by actuating of the volume modulator 30. As the volume of the gas reservoir 22 is modified the gas pressure inside the gas reservoir 22 will be subject to a corresponding modification. The pressure change resulting from the volume modification is measured in step 106. If the volume in step 104 is reduced, the pressure to be measured in step 106 will increase. If the volume in step 104 is increased, the pressure to be measured in step 106 will decrease.

Thereafter the total volume of the liquid reservoir is calculated in step 108 in accordance to the formula as given above.

LIST OF REFERENCE NUMBERS

1 drug delivery device
2 housing
10 measuring arrangement
12 flexible bag
14 liquid medium
15 gaseous medium
16 membrane
20 container
21 interior volume
22 gas reservoir
24 liquid reservoir
25 separation wall
26 sidewall
27 end wall
28 pressure sensor
29 end wall
30 volume modulator
31 piston
32 guiding section
34 drive
40 controller
42 outlet 44 control valve
45 tubing
46 suction pump
50 regulator
110 measuring arrangement
120 container
121 interior volume
122 gas reservoir
123 first container part
125 second container part
130 volume modulator
132 guiding section
136 display
138 actuation member
210 measuring arrangement

The invention claimed is:

1. A measuring arrangement for measuring a volume occupied by a liquid medium inside a liquid reservoir of a drug delivery device, the measuring arrangement comprising:
 a container having an interior volume containing a gas reservoir filled with a gaseous medium and containing the liquid reservoir filled with the liquid medium, wherein the gas reservoir and the liquid reservoir are hermetically separated by an impenetrable separation wall;
 a volume modulator to induce a volume change of the gas reservoir;
 a pressure sensor arranged inside the gas reservoir to measure a pressure change of the gaseous medium in response to the volume change of the gas reservoir;
 a controller connectable to the pressure sensor, wherein the controller is configured to calculate the volume of the liquid reservoir on the basis of the pressure change and the volume change;
 an outlet extending through the container and being in fluid connection with the liquid reservoir; and
 a suction pump in fluid connection with the outlet,
 wherein the container comprises at least a first container part and a second container part that are detachably connectable and sealingly engageable in a gas tight and fluid tight manner to form the interior volume,
 wherein the liquid reservoir is arranged in the second container part and is formed and completely confined by a flexible bag filled with the liquid medium,
 wherein only the outlet or only a tube connected to the outlet is in fluid connection with an interior of the flexible bag, and
 wherein the separation wall between the liquid reservoir and the gas reservoir is formed by the flexible bag.

2. The measuring arrangement according to claim 1, wherein the volume modulator comprises a piston slidably arranged in a longitudinally extending guiding section of a side wall of the container.

3. The measuring arrangement according to claim 2, wherein the piston is displaceable along the guiding section by a drive.

4. The measuring arrangement according to claim 1, wherein the outlet is selectively lockable by a control valve and/or by the suction pump.

5. The measuring arrangement according to claim 4, wherein at least one of the control valve and the suction pump is controllable by a regulator connectable or connected to the controller.

6. The measuring arrangement according to claim 1, wherein the volume occupied by the liquid medium is calculated using at least one of: an available interior volume of the container, the volume change of the gas reservoir, the pressure change inside the gas reservoir, and an initial pressure inside the gas reservoir.

7. The measuring arrangement according to claim 6, wherein the volume occupied by the liquid medium is calculated as being the available interior volume of the container or being the volume change of the gas reservoir.

8. The measuring arrangement according to claim 1, wherein the impenetrable separation wall between the liquid reservoir and the gas reservoir comprises a flexible membrane.

9. The measuring arrangement according to claim 1, wherein the volume modulator and the pressure sensor are arranged in the first container part.

10. A method of measuring a volume occupied by a liquid medium inside a liquid reservoir arranged inside a container, wherein the container further contains a gas reservoir filled with a gaseous medium, and wherein the method comprises:
 inducing a volume change of the gas reservoir;
 measuring a pressure change in the gas reservoir, using a measurement arrangement of claim 1, in response to the volume change of the gas reservoir; and
 calculating the volume of the liquid reservoir based on the pressure change and the volume change.

11. The drug delivery device according to claim 1, wherein the flexible bag is entirely surrounded by the gas reservoir.

12. A drug delivery device comprising:
 a housing;
 a suction pump; and
 a measuring arrangement for measuring a volume occupied by a liquid medium inside a liquid reservoir, the measuring arrangement comprising:
  a container having an interior volume containing a gas reservoir filled with a gaseous medium and containing the liquid reservoir filled with the liquid medium, wherein the gas reservoir and the liquid reservoir are hermetically separated by an impenetrable separation wall,
  a volume modulator to induce a volume change of the gas reservoir,
  a pressure sensor arranged inside the gas reservoir to measure a pressure change of the gaseous medium in response to the volume change of the gas reservoir,
  a controller connectable to the pressure sensor, wherein the controller is configured to calculate the volume of the liquid reservoir on the basis of the pressure change and the volume change, and
  an outlet extending through the container and being in fluid connection with the liquid reservoir, wherein the suction pump is in fluid connection with the outlet,
 wherein the container comprises at least a first container part and a second container part that are detachably connectable and sealingly engageable in a gas tight and fluid tight manner to form the interior volume,
 wherein the liquid reservoir is arranged in the second container part and is formed and completely confined by a flexible bag filled with the liquid medium,
 wherein only the outlet or only a tube connected to the outlet is in fluid connection with an interior of the flexible bag, and
 wherein the separation wall between the liquid reservoir and the gas reservoir is formed by the flexible bag.

13. The drug delivery device according to claim 12, wherein the at least one of the first container part and the second container part forms at least a portion of the housing.

14. The drug delivery device according to claim 12, wherein the drug delivery device is configured as an infusion pump or as an infusion system.

15. The drug delivery device according to claim 12, wherein the drug delivery device is configured as an injection device.

* * * * *